(12) United States Patent
Gruber et al.

(10) Patent No.: US 6,221,876 B1
(45) Date of Patent: Apr. 24, 2001

(54) METHODS FOR INHIBITING MRP1

(75) Inventors: Joseph Michael Gruber, Brownsburg, IN (US); Sean P Hollinshead, Durham, NC (US); Bryan H Norman, Indianapolis, IN (US); Joseph W Wilson, Durham, NC (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/646,063

(22) PCT Filed: Apr. 7, 1999

(86) PCT No.: PCT/US99/07615

§ 371 Date: Sep. 13, 2000

§ 102(e) Date: Sep. 13, 2000

(87) PCT Pub. No.: WO99/51236

PCT Pub. Date: Oct. 14, 1999

Related U.S. Application Data

(60) Provisional application No. 60/081,088, filed on Apr. 8, 1998.

(51) Int. Cl.[7] .......................... A61K 31/47; C07D 498/04
(52) U.S. Cl. ............................................... 514/293; 546/83
(58) Field of Search ................................. 546/83; 514/293

(56) References Cited

U.S. PATENT DOCUMENTS 5,451,585 * 9/1995 Albaugh ................................ 514/282

* cited by examiner

*Primary Examiner*—Bernard Dentz
(74) *Attorney, Agent, or Firm*—Elizabeth A. Dewalt; Gilbert Voy

(57) ABSTRACT

The present invention relates to a compound of formula (I) which is useful for inhibiting neoplasms where the resistance is conferred in part or in total by MRP1.

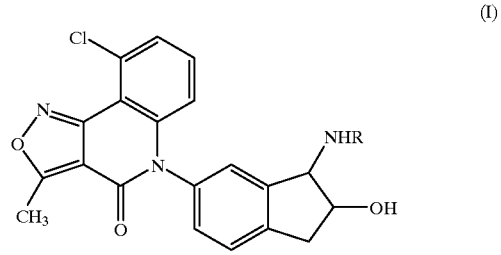

(I)

15 Claims, No Drawings

METHODS FOR INHIBITING MRP1

This application is a 371 of PCT/US99/07615 filed Apr. 7, 1999 which claims priority from Provisional Application No. 60/081,088 filed Apr. 8, 1998.

Along with surgery and radiotherapy, chemotherapy continues to be an effective therapy for many cancers. In fact, several types of cancer are now considered to be curable by chemotherapy and include Hodgkin's disease, large cell lymphoma, acute lymphocytic leukemia, testicular cancer and early stage breast cancer. Other cancers such as ovarian cancer, small cell lung and advanced breast cancer, while not yet curable, are exhibiting positive response to combination chemotherapy.

One of the most important unsolved problems in cancer treatment is drug resistance. After selection for resistance to a single cytotoxic drug, cells may become cross resistant to a whole range of drugs with different structures and cellular targets, e.g., alkylating agents, antimetabolites, hormones, platinum-containing drugs, and natural products. This phenomenon is known as multidrug resistance (MDR). In some types of cells, this resistance is inherent, while in others, such as small cell lung cancer, it is usually acquired.

Such resistance is known to be multifactorial and is conferred by at least two proteins: the 170 kDa P-glycoprotein (MDR1) and the more recently identified 190 kDa multidrug resistance protein (MRP1). Although both MDR1 and MRP1 belong to the ATP-binding cassette superfamily of transport proteins, they are structurally very different molecules and share less than 15% amino acid homology. Despite the structural divergence between the two proteins, by 1994 there were no known consistent differences in the resistance patterns of MDR1 and MRP1 cell lines. However, the association, or lack thereof, of MRP1 and resistance to particular oncolytics is known. See Cole, et. al., Pharmacological Characterization of Multidrug Resistant MRP-transfected Human Tumor Cells, *Cancer Research,* 54:5902–5910, 1994. Doxorubicin, daunorubicin, epirubicin, vincristine, and etoposide are substrates of MRP1, i.e., MRP1 can bind to these oncolytics and redistribute them away from their site of action, the nucleus, and out of the cell. Id. and Marquardt, D., and Center, M. S., *Cancer Research,* 52:3157, 1992.

Doxorubicin, daunorubicin, and epirubicin are members of the anthracycline class of oncolytics. They are isolates of various strains of Streptomyces and act by inhibiting nucleic acid synthesis. These agents are useful in treating neoplasms of the bone, ovaries, bladder, thyroid, and especially the breast. They are also useful in the treatment of acute lymphoblastic and myeloblastic leukemia, Wilm's tumor, neuroblastoma, soft tissue sarcoma, Hodgkin's and non-Hodgkin's lymphomas, and bronchogenic carcinoma.

Vincristine, a member of the vinca alkaloid class of oncolytics, is an isolate of a common flowering herb, the periwinkle plant (Vinca rosea Linn). The mechanism of action of vincristine is still under investigation but has been related to the inhibition of microtubule formation in the mitotic spindle. Vincristine is useful in the treatment of acute leukemia, Hodgkin's disease, non-Hodgkin's malignant lymphomas, rhabdomyosarcoma, neuroblastoma, and Wilm's tumor.

Etoposide, a member of the epipodophyllotoxin class of oncolytics, is a semisynthetic derivative of podophyllotoxin. Etoposide acts as a topoisomerase inhibitor and is useful in the therapy of neoplasms of the testis, and lung.

It is presently unknown what determines whether a cell line will acquire resistance via a MDR1 or MRP1 mechanism. Due to the tissue specificity of these transporters and/or in the case where one mechanism predominates or is exclusive, it would be useful to have a selective inhibitor of that one over the other. Furthermore, when administering a drug or drugs that are substrates of either protein, it would be particularly advantageous to co-administer an agent that is a selective inhibitor of that protein. It is, therefore, desirable to provide compounds which are selective inhibitors of MDR1 or MRP1.

The present invention relates to a compound of formula I:

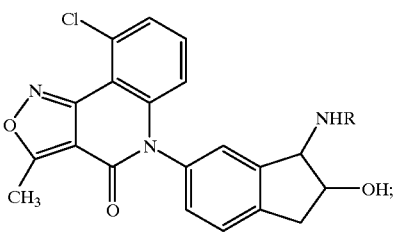

where:

R is hydrogen, $COR^1$, $SO_2R^2$, or a moiety of the formula

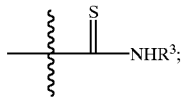

$R^1$ is $C_1$–$C_4$ alkyl, aryl, substituted aryl, furanyl, indolyl, thiophenylmethyl, 5-methylisoxazolyl, $NHR^4$, or $CHR^5OR^6$;

$R^2$ is 3,5-dimethylisoxazolyl or phenyl where the phenyl group is optionally substituted once with nitro, $C_1$–$C_4$ alkyl, trifluoromethyl, $C_1$–$C_4$ alkoxy, $C_2$–$C_4$ alkanoyl, carbo($C_1$–$C_4$ alkoxy), or amino($C_1$–$C_4$ alkyl);

$R^3$ is phenyl where the phenyl group is optionally substituted once with trifluoromethyl or N-acetylamino;

$R^4$ is hydrogen, $C_1$–$C_6$ alkyl, or phenyl where the phenyl group is optionally substituted once with nitro, $C_1$–$C_4$ alkyl, trifluoromethyl, $C_1$–$C_4$ alkoxy, $C_2$–$C_4$ alkanoyl, carbo($C_1$–$C_4$ alkoxy), or amino($C_1$–$C_4$ alkyl);

$R^5$ is hydrogen, $C_1$–$C_4$ alkyl, or phenyl; and $R^6$ is phenyl or acetyl; or a pharmaceutical salt or solvate thereof.

The present invention further relates to a method of inhibiting MRP1 in a mammal which comprises administering to a mammal in need thereof an effective amount of a compound of formula I, or a pharmaceutical salt or solvate thereof.

In another embodiment, the present invention relates to a method of inhibiting a resistant neoplasm, or a neoplasm susceptible to resistance in a mammal which comprises administering to a mammal in need thereof an effective amount of a compound of formula I, or a pharmaceutical salt or solvate thereof, in combination with an effective amount of an oncolytic agent.

The present invention also relates to a pharmaceutical formulation comprising a compound of formula I, or a pharmaceutical salt or solvate thereof, in combination with one or more oncolytics, pharmaceutical carriers, diluents, or excipients therefor.

The current invention concerns the discovery that a select group of compounds, those of formula I, are selective inhibitors of multidrug resistant protein (MRP1) and are thus useful in treating MRP1 conferred multidrug resistance (MDR) in a resistant neoplasm and a neoplasm susceptible to resistance.

The term "inhibit" as it relates to MRP1 and "inhibiting" MRP1' refer to prohibiting, alleviating, ameliorating, halting, restraining, slowing or reversing the progression of, or reducing MRP1's ability to redistribute an oncolytic away from the oncolytic's site of action, most often the neoplasm's nucleus, and out of the cell.

As used herein, the term "effective amount of a compound of formula I" refers to an amount of a compound of the present invention which is capable of inhibiting MRP1. The term "effective amount of an oncolytic" refers to an amount of oncolytic capable of inhibiting a neoplasm, resistant or otherwise.

The term "inhibiting a resistant neoplasm, or a neoplasm susceptible to resistance" refers to prohibiting, halting, restraining, slowing or reversing the progression of, reducing the growth of, or killing resistant neoplasms and/or neoplasms susceptible to resistance.

The term "resistant neoplasm" refers to a neoplasm which is resistant to chemotherapy where that resistance is conferred in part, or in total, by MRP1. Such neoplasms include, but are not limited to, neoplasms of the bladder, bone, breast, lung(small-cell), testis, and thyroid and also includes more particular types of cancer such as, but not limited to, acute lymphoblastic and myeloblastic leukemia, Wilm's tumor, neuroblastoma, soft tissue sarcoma, Hodgkin's and non-Hodgkin's lymphomas, and bronchogenic carcinoma.

A neoplasm which is "susceptible to resistance" is a neoplasm where resistance is not inherent nor currently present but can be conferred by MRP1 after chemotherapy begins. Thus, the methods of this invention encompass a prophylactic and therapeutic administration of a compound of formula I.

The term "chemotherapy" refers to the use of one or more oncolytics where at least one oncolytic is a substrate of MRP1. A "substrate of MRP1" is an oncolytic that binds to MRP1 and is redistributed away from the oncolytics site of action, (the neoplasm's nucleus) and out of the cell, thus, rendering the therapy less effective.

The terms "treat" or "treating" bear their usual meaning which includes preventing, prohibiting, alleviating, ameliorating, halting, restraining, slowing or reversing the progression, or reducing the severity of MRP1 derived drug resistance in a multidrug resistant tumor.

The compounds of formula I contain at least 2 chiral centers which are located at the 1 and 2 positions of the indane ring system. The enantiomers with the absolute stereochemistry of R,R or S,S are contemplated within the scope of the present invention. That is, compounds of formula I whose substituents at the 1 and 2 position of the indane ring that have a trans relationship to one another are contemplated within the scope of the present invention.

In the general formulae of the present document, the general chemical terms have their usual meanings. For example, the term "$C_1$–$C_3$ alkyl" refers to methyl, ethyl, propyl, isopropyl, and cyclopropyl. The term "$C_1$–$C_4$ alkyl" encompasses $C_1$–$C_3$ alkyl groups and also refers to butyl, cyclobutyl, s-butyl, and t-butyl. The term "$C_1$–$C_6$ alkyl" includes $C_1$–$C_4$ alkyl groups and also refers to monovalent, straight, branched, or cyclic saturated hydrocarbon chains containing 5 or 6 carbon atoms including, but not limited to, cyclopentyl, pentyl, hexyl, cyclohexyl, and the like.

The term "$C_2$–$C_4$ alkanoyl" refers to a $C_1$–$C_3$ alkyl group attached through a carbonyl moiety.

The term "$C_1$–$C_4$ alkoxy" refers to a $C_1$–$C_4$ alkyl group attached through an oxygen atom.

The term "halo" or "halide" refers to fluoro, chloro, bromo, or iodo.

The term "aryl" refers to phenyl, benzyl, and napthyl.

The term "substituted aryl" refers to a phenyl, benzyl, and napthyl group, respectively, which is para substituted with a $C_1$–$C_4$ alkyl, $C_1$–$C_4$ alkoxy, or halo group or is substituted independently three times with a $C_1$–$C_4$ alkoxy group.

The term "amino protecting group" as used in this specification refers to a substituent(s) of the amino group commonly employed to block or protect the amino functionality while reacting other functional groups on the compound. Examples of such amino-protecting groups include the formyl group, the trityl group, the phthalimido group, the acetyl group, the trichloroacetyl group, the chloroacetyl, bromoacetyl, and iodoacetyl groups, urethane-type blocking groups such as benzyloxycarbonyl, 9-fluorenylmethoxycarbonyl ("FMOC"), and the like; and like amino protecting groups. The species of amino protecting group employed is not critical so long as the derivatized amino group is stable to the condition of subsequent reaction (s) on other positions of the molecule and can be removed at the appropriate point without disrupting the remainder of the molecule. Similar amino protecting groups used in the cephalosporin, penicillin, and peptide arts are also embraced by the above terms. Further examples of groups referred to by the above terms are described by T. W. Greene, *Protective Groups in Organic Synthesis,* John Wiley and Sons, New York, N.Y., 1991, Chapter 7 hereafter referred to as *Greene.* A preferred amino protecting group is t-butyloxycarbonyl.

The term "carbonyl activating group" refers to a substituent of a carbonyl that renders that carbonyl prone to nucleophilic addition. Suitable activating groups are those which have a net electron withdrawing effect on the carbonyl. Such groups include, but are not limited to, alkoxy, aryloxy, nitrogen containing aromatic heterocycles, or amino groups such as oxybenzotriazole, imidazolyl, nitrophenoxy, pentachlorophenoxy, N-oxysuccinimide, N,N'-dicyclohexylisoure-O-yl, N-hydroxy-N-methoxyamino, and the like; acetates, formates, sulfonates such as methanesulfonate, ethanesulfonate, benzenesulfonate, or p-toluenylsulfonate, and the like; and halides especially chloride, bromide, or iodide.

In general, the term "pharmaceutical" when used as an adjective means substantially non-toxic to living organisms. For example, the term "pharmaceutical salt" as used herein, refers to salts of the compounds of formula I which are substantially non-toxic to living organisms. See, e.g., Berge, S. M, Bighley, L. D., and Monkhouse, D. C., pharmaceutical salts include those salts prepared by reaction of the compounds of formula I with an inorganic or organic acid. Such salts are known as acid addition salts. These pharmaceutical salts frequently have enhanced solubility characteristics compared to the compound from which they are derived, and thus are often more amenable to formulation as liquids or emulsions.

Examples of pharmaceutical acid addition salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, ethanesulfonate, propanesulfonate, naphthalene-1-sulfonate, napthalene-2-sulfonate, mandelate, and the like of a compound of formula I.

The term "solvate" represents an aggregate that comprises one or more molecules of the solute, such as a formula I compound, with one or more molecules of solvent.

The term "suitable solvent" refers to a solvent which is inert to the ongoing reaction and sufficiently solubilizes the reactants to effect the desired reaction. Examples of suitable solvents include but are not limited to, dichloromethane, chloroform, 1,2-dichloroethane, diethyl ether, acetonitrile, ethyl acetate, 1,3-dimethyl-2-imidazolidinone, tetrahydrofuran, dimethylformamide, toluene, chlorobenzene, dimethylsulfoxide, mixtures thereof, and the like.

The term "carbonyl activating reagent" refers to a reagent that converts the carbonyl of a carboxylic acid group to one that is more prone to nucleophilic addition and includes, but is not limited to, such reagents as those found in The Peptides, Gross and Meienhofer, Eds., Academic Press (1979), Ch. 2 and M. Bodanszky, *Principles of Peptide Synthesis*, 2$^{nd}$ Ed., Springer-Verlag Berlin Heidelberg, 1993, hereafter referred to as The Peptides and Peptide Synthesis respectively. Specifically, carbonyl activating reagents include nucleophilic sources of a halogen such as, thionyl bromide, thionyl chloride, oxalyl chloride, and the like; alcohols such as nitrophenol, pentachlorophenol, and the like; amines such as N-hydroxy-N-methoxyamine and the like; acid halides such as acetic, formic, methanesulfonic, ethanesulfonic, benzenesulfonic, or p-tolenesulfonic acid halide, and the like; and compounds such as 1,1'-carbonyldiimidazole, benzotriazole, imidazole, N-hydroxysuccinimide, dicyclohexylcarbodiimide, and the like.

The term "suitable thermodynamic base" refers to a base which acts as a proton trap for any protons which may be produced as a byproduct of the desired reaction or to a base which provides a reversible deprotonation of an acidic substrate and is reactive enough to effect the desired reaction without significantly effecting any undesired reactions. Examples of thermodynamic bases include, but are not limited to, carbonates, bicarbonates, and hydroxides (e.g., lithium, sodium, or potassium carbonate, bicarbonate, or hydroxide), tri-($C_1$–$C_4$ alkyl)amines, or aromatic nitrogen containing heterocycles (e.g., pyridine).

While all of the compounds of the present invention are useful, certain of the compounds are particularly interesting and are preferred. The following listing sets out several groups of preferred compounds, formulations, and methods. It will be understood that each of the listings may be combined with other listings to create additional groups of preferred embodiments.

a) R is $COR^1$;
b) R is $SO_2R^2$;
c) $R^1$ is phenyl;
d) $R^1$ is benzyl;
e) $R^1$ is 3,4,5-trimethoxyphenyl;
f) $R^1$ is 3,4,5-trimethoxybenzyl;
g) $R^2$ is phenyl;
h) $R^2$ is 4-methoxyphenyl;
i) $R^2$ is 3,5-dimethoxyisoxazole;
j) The compound is a pharmaceutical salt;
k) The compound is the hydrochloride salt;
l) The compounds of the Examples section;
m) The method where the mammal is a human;
n) The method where the oncolytic(s) is selected from: doxorubicin, daunorubicin, epirubicin, vincristine, and etoposide;
o) The method where the neoplasm is of the Wilm's type, bladder, bone, breast, lung(small-cell), testis, or thyroid or the neoplasm is associated with acute lymphoblastic and myeloblastic leukemia, neuroblastoma, soft tissue sarcoma, Hodgkin's and non-Hodgkin's lymphomas, or bronchogenic carcinoma;
p) The formulation where the oncolytic(s) is selected from the group: doxorubicin, daunorubicin, epirubicin, vincristine, and etoposide;
q) The compound is the R isomer;
r) The compound is the S isomer; and
s) The compound is a mixture of isomers.

The compounds of the present invention can be prepared by a variety of procedures, including solid phase or solution phase synthetic techniques. Solid phase techniques are illustrated below in Scheme 1. The particular order of steps required to produce the compounds of formula I is dependent upon the particular compound being synthesized, the starting compound, and the relative lability of the substituted moieties.

The reactions of Scheme 1 are all performed in the solid phase. That is, the molecule that is manipulated in the various conversions is bound to an insoluble polystyrene resin and the reagents used to modify or add to the bound molecule are soluble. A general strategy for syntheses of this kind, which is applicable to this case, is to employ large molar excesses of unbound reagents, relative to the bound reagent, in order to insure complete conversion of the bound molecule. When the conversion is substantially complete, the soluble reagents can simply be filtered away. The impure resin which will contain residues of the just finished reaction can be cleaned simply by rinsing the impure resin with, for example, the same solvent employed in the reaction. For example, if the reaction was performed in tetrahydrofuran, you can rinse the resin with pure tetrahydrofuran. These principles are applicable to all the reactions discussed in Scheme 1.

Compounds of formula I may be prepared as illustrated in Scheme 1 below, where PS is a polystyrene resin, $R^5$ is a carbonyl activating group, and R, $R^1$, $R^2$, and $R^3$ are as described supra.

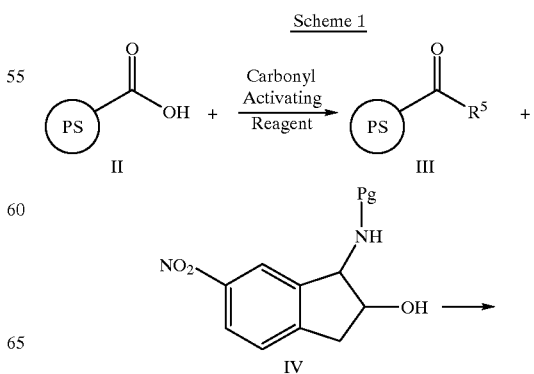

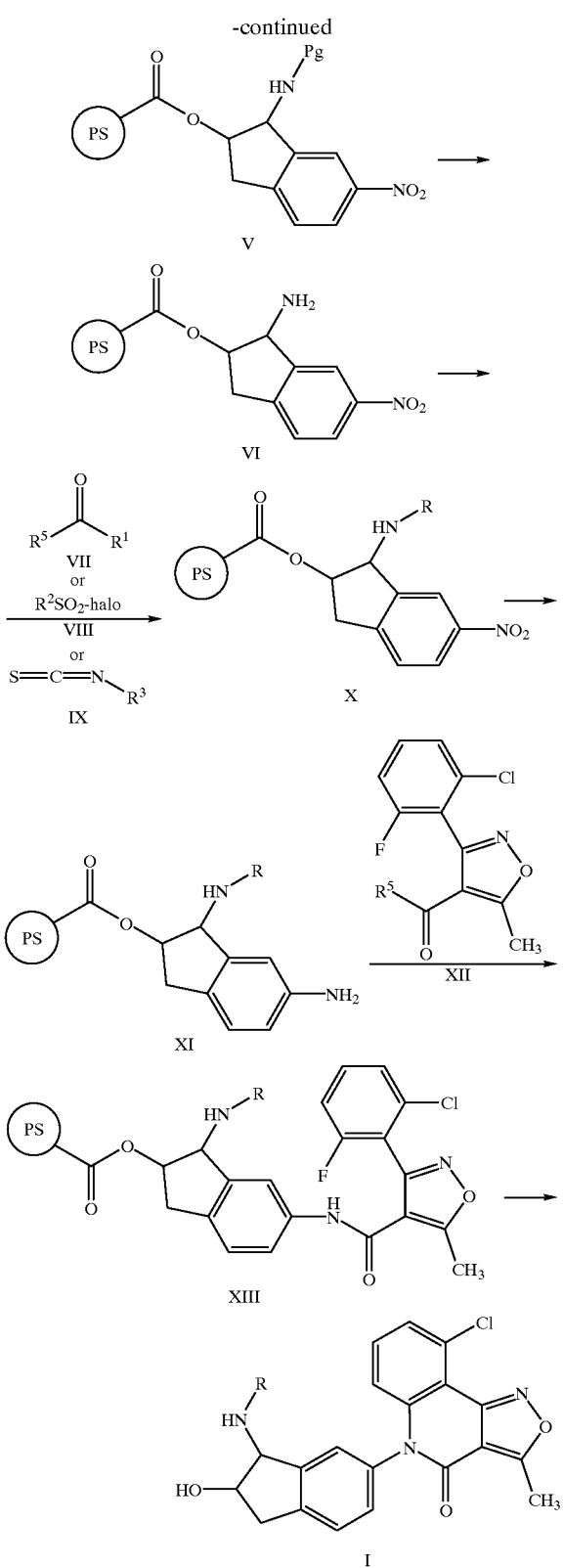

Acids of formula II may be activated to form the activated carboxylic acids of formula III by methods well known in the chemical arts. See, e.g., The Peptides or Peptide Synthesis for general discussions of solution phase activation and Preparations sections below for solid phase activation. Specifically, the compounds of formula III are typically prepared by exposing a carboxylated polystyrene resin to a molar excess of activating reagent in a suitable solvent. A convenient and preferred solvent for this purpose is a mixture of dichloromethane and dimethylformamide. Oxalyl chloride is typically a preferred and convenient activating reagent and a 3 molar excess of this activating reagent is generally employed. Usually the reaction is performed at the reflux temperature of the mixture for about 24 hours.

The resin bound esters of formula V may be prepared from compounds of formula IV and resin bound activated acids of formula III by methods very well known in the chemical arts. For a general instruction on the solution phase conversion of activated carboxylic acids to esters see, e.g., Larock, *Comprehensive Organic Transformations*, pgs. 978–979, VCH Publishers, New York, N.Y., 1989, hereafter referred to as Larock. Specifically, the ester of formula III in the presence of a thermodynamic base, optionally in the presence of a thermodynamic base, and optionally in the presence of dimethylamino pyridine (DMAP), may be exposed to the compound of formula IV. Tetrahydrofuran is typically a convenient and preferred solvent. DMAP is preferably employed in a catalytic fashion, typically in about a 50 molar percent relative to the bound material. The compound of formula IV, however, is employed in an excess, usually in about a 1.4 to about a 2.5 molar excess. A preferred base is pyridine and is usually employed in large molar excesses, typically on the order of about a 20 molar excess. Once all the reagents are combined, the reaction is usually allowed to proceed at the reflux temperature of the mixture for 8 to 12 days.

The amino protecting group contained in the compound of formula V may now be removed to form the compounds of formula VI. Choices of protecting groups and reagents and methods available to install or remove them may be found in the Greene reference cited above. Preferred protecting groups and methods for their removal may be found in the Preparations section below.

The resin bound free amine of formula VI in the presence of a suitable solvent, optionally in the presence of a thermodynamic base, and optionally in the presence of dimethylamino pyridine (DMAP), may now be treated with a compound of formula VII to provide a compound of formula X where R is $COR^1$. Typically a preferred and convenient solvent is dichloromethane. When a base is employed, pyridine is typically a preferred base. Furthermore, when a base is employed, the base and compound of formula VII are typically employed in large stoichiometric excesses relative to the resin bound material. For example the base is typically employed in between a 15 and 20 molar excess while the compound of formula IV is generally employed in between a 5 to 8 molar excess. When a base is not employed, the compound of formula VII is typically employed in a relatively larger stoichiometric excess. The reaction is usually performed at a temperature range of about 0° C. to about the reflux temperature of the solvent for from 10 minutes to 18 hours. Preferably, the reaction is performed at about 15° C. to about 40° C. for from 12 to 24 hours and most preferred is at room temperature for 18 hours.

Under the same conditions as the previous paragraph, a compound of formula VI may alternatively be treated with a compound of formula VIII or IX to afford, respectively, the compounds of formula X where R is $SO_2R^2$ or a moiety of the formula

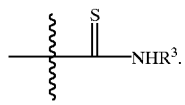

In the next reaction of Scheme 1, the nitro group at the 2 position of the indane ring is reduced to an amino moiety resulting in the compounds of formula XI. Methods of reducing a nitro group to an amine are well known. See, e.g., Larock at 412–415 or the Preparations and Examples sections below. Usually, the transformation is accomplished by exposing the resin bound compound of formula X to a large molar excess of reducing agent in a suitable solvent. Dimethylformamide is typically a convenient and preferred solvent for this purpose. Tin(II) chloride dihydrate is usually the preferred reducing agent. The reaction is usually performed at a temperature range of about 0° C. to about the reflux temperature of the solvent for from 12 hours to 72 hours. Preferably, the reaction is performed at about 15° C. to about 40° C. for from 30 to 60 hours and most preferred is at room temperature for 48 hours.

The next reaction of Scheme 2 is an acylation of the amino moiety formed in the previous reaction to form the compounds of formula XIII. This acylation has the same reaction and reagent profiles of the conversion of compounds of formula VI to compounds of formula X except that in this case, the only acylating agent used is the compound of formula XII, i.e., a 3-(2-chloro-6-fluorophenyl)-5-methylisoxaz-4-oyl activated acid.

Finally, the compound of formula XIII may be cyclized and freed from the resin to form the compound of formula XIV. This transformation may be accomplished by exposing the resin bound compound of formula XIII to a suitable thermodynamic base in a suitable solvent. Typically a preferred and convenient solvent is tetrahydrofuran. Usually a convenient and preferred thermodynamic base is sodium hydroxide added as a 2N solution in methanol. The reaction is typically performed at about 15° C. to about the reflux temperature of the mixture for from 30 minutes to about 18 hours. Preferably, the reaction is performed at room temperature for about 18 hours. The base is typically employed in a large molar excess, usually in about a 10 to about a 15 molar excess relative to the compound of formula XIV. Preferably, about a 11 to about a 13 molar excess is typically employed.

Any amino protecting groups found in the cyclized compounds of formula I may optionally be removed as taught in Greene to provide the free amine. Preferred choices of protecting groups and methods for their removal may be found in the Preparations and Examples sections which follow.

The pharmaceutical salts of the invention are typically formed by reacting a compound of formula I with an equimolar or excess amount of acid. The reactants are generally combined in a mutual solvent such as diethylether, tetrahydrofuran, methanol, ethanol, isopropanol, benzene, and the like. The salts normally precipitate out of solution within about one hour to about ten days and can be isolated by filtration or other conventional methods.

Acids commonly employed to form pharmaceutical acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like. Preferred pharmaceutical acid addition salts are those formed with mineral acids such as hydrochloric acid, hydrobromic acid, and sulfuric acid, and those formed with organic acids such as maleic acid, tartaric acid, and methanesulfonic acid.

It should be recognized that the particular counterion forming a part of any salt of this invention is not of a critical nature, so long as the salt as a whole is pharmacologically acceptable and as long as the counterion does not contribute undesired qualities to the salt as a whole.

Compounds of formula II, IV, VII, VIII, IX, and XII are known in the art and, to the extent not commercially available, are readily synthesized by standard procedures commonly employed in the art. For example, the compounds of formula IV may be prepared as taught in the Preparations section below.

The optimal time for performing the reactions of Scheme 1 can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The intermediate compounds of this invention are preferably purified before their use in subsequent reactions. Purification of the intermediates typically entails washing the resin as discussed above. The compounds of formula I may be purified by their crystallizing out of the reaction solution during their formation. These compounds can then be collected by filtration. Alternatively, the reaction solvent may be removed by extraction, evaporation, or decantation. These final products of formula I may be further purified, if desired by common techniques such as recrystallization or chromatography over solid supports such as silica gel or alumina.

The following Preparations and Examples are provided to better elucidate the practice of the present invention and should not be interpreted in any way as to limit the scope of same. Those skilled in the art will recognize that various modifications may be made while not departing from the spirit and scope of the invention. All publications mentioned in the specification are indicative of the level of those skilled in the art to which this invention pertains. The terms and abbreviations used in the instant Preparations and Examples have their normal meanings unless otherwise designated. For example ° C., N, mmol, g, mL, M, HPLC, MS(IS), MS(FAB), and H NMR, refer to degrees Celsius, normal or normality, millimole or millimoles, gram or grams, milliliter or milliliters, molar or molarity, high performance liquid chromatography, ion spray mass spectrometry, fast atom bombardment mass spectrometry, and proton nuclear magnetic resonance spectrometry respectively.

Preparations

Preparation 1

6-Nitro-1-Indanone

To a solution of 1-indanone (25.0 g, 189 mmol) in concentrated sulfuric acid (84 mL) at 0° C. was added a solution of potassium nitrate (8.33 g, 82.4 mmol) in sulfuric acid (40 mL) at a rate sufficient to maintain an internal temperature below 15° C. After the addition was complete, the reaction was allowed to stir at 0° C. for 1 hour. The reaction mixture was then poured into crushed ice and stirred vigorously for 30 minutes. The suspension was then filtered, air dried, and purified by liquid chromatography (50 ethyl acetate/toluene) to provide 18.90 g of the title compound. (56%).

Preparation 2

6-Nitro-1-Indanol

A solution of 6-nitro-1-indanone (18.9 g, 107 mmol) in methanol (300 mL) was cooled to 0° C. and sodium borohydride (4.04 g, 107 mmol) was added in several small portions. The reaction was then stirred overnight at 25° C. The solution was quenched at 0° C. with methanolic hydrochloric acid (200 mL), concentrated under reduced pressure, redissolved in dichloromethane, washed with water, and the organic layer reconcentrated to provide the crude alcohol as a brown solid which was used without further purification in Preparation 3.

Preparation 3

6-Nitro-1-Indene

To a solution of 6-nitro-1-indanol in toluene (300 mL) was added a catalytic amount of p-toluenesulfonic acid and the reaction was refluxed for 1 hour using a Dean Stark trap to remove the water. The organic layer was washed with saturated aqueous sodium bicarbonate (3×200 mL), dried over magnesium sulfate, filtered, and the filtrate solvent removed under vacuum. The crude residue was crystallized from methanol to afford 13.41 g of the title compound. (78% over two steps).

Preparation 4

6-Nitro-1,2-Epoxyindane

To a solution of 6-nitro-1-indene (10.5 g, 65.3 mmol) in dichloromethane (350 mL) at 0° C. was added meta chloroperbenzoic acid (29.0 g, 92.4 mmol) in small amounts over the course of 1 hour. After stirring overnight at 25° C., the mixture was washed with saturated aqueous sodium sulfite (2×200 mL) and saturated aqueous sodium bicarbonate (2×200 mL), filtered through a cotton plug, and concentrated under vacuum to give the title compound which was used in Preparation 5 without further purification.

Preparation 5

Trans-6-Nitro-1-Amino-2-Hydroxyindane

A suspension of 6-nitro-1,2-epoxyindane in concentrated ammonium hydroxide (250 mL) was heated overnight in an oil bath at 45° C. The next day water was added and the basic aqueous layer was saturated with sodium chloride. The cloudy reaction mixture was extracted with tetrahydrofuran until no more product could be seen in the aqueous layer by TLC. The organic layers were combined, dried over magnesium sulfate, filtered, concentrated, and recrystallized from ethyl acetate to give 11.54 g of the title compound. (91% over two steps).

Preparation 6

Trans-N-t-Butyloxycarbonyl-6-Nitro-1-Amino-2-Hydroxyindane

To a solution of trans-6-nitro-1-amino-2-hydroxyindane (8.34 g, 42.9 mmol) in tetrahydrofuran (200 mL) was added a solution of di-t-butyldicarbonate (11.3 g, 51.5 mol) in tetrahydrofuran (50 mL). After stirring 1 hour at 25° C., the solvent was removed under reduced pressure and the resulting solid was recrystallized from ethyl acetate to afford 11.37 g of the title compound. (90%).

Preparation 7

Solid Phase Synthesis of Trans O-Resin Bound 1-Amino-2-Hydroxy-6-Nitroindane

Step 1: Activation of the Resin/Binding to the Resin—Trans O-Resin Bound N-t-Butyloxycarbonyl-1-Amino-2-Hydroxy-6-Nitroindane Under an nitrogen atmosphere, a 3 L three-necked round bottomed flask equipped with an overhead stirrer and addition funnel was charged with carboxylated polystyrene resin (70 g, 2.8 mmol $CO_2H$/g resin), anhydrous dichloromethane (1 L), and anhydrous dimethylformamide (10 mL). Next, oxalyl chloride (50.8 mL, 582 mmol) was added via a slow dropwise addition from an addition funnel. After refluxing overnight under nitrogen, the solvent was removed under vacuum using a gas dispersion tube. The resin was subsequently washed with anhydrous dichloromethane (3×500 mL). Once the last wash was complete, the resin was dried under vacuum for 2 to 3 hours. At this time, the polymer was resuspended in dry tetrahydrofuran (1 L) followed by the addition of dry pyridine (314 mL, 3.88 mol), DMAP (12 g, 97 mmol), and trans O-resin bound 1-amino-2-hydroxy-6-nitroindane (85.6 g, 291 mmol). The mixture was refluxed for 10 days under an inert atmosphere. The solvent was removed by vacuum filtration and the resin was washed with tetrahydrofuran (3×300 mL), dichloromethane (3×300 mL), and dried overnight in a vacuum oven to provide 122.18 g of the title compound as a tan resin.

Step 2: Deprotection—Trans O-Resin Bound 1-Amino-2-Hydroxy-6-Nitroindane

Into a round bottomed flask equipped with a stir bar was placed the trans O-resin bound N-t-butyloxycarbonyl-1-amino-2-hydroxy-6-nitroindane (28 mg, 0.028 mmol), 500 μl dichloromethane, and trifluoroacetic acid (109 μl, 0.141 mmol). The reaction mixture was stirred at 25° C. overnight. The resin was then collected by filtration, resuspended in 10% triethylamine/dichloromethane, stirred for 15 minutes, filtered again, and finally washed with dichloromethane to afford the title compound.

General Procedure for Preparations 8–36

Trans O-Resin bound N-"R"-(Isoxazolo[3,4-c]-1,2-Dihydro-3-methyl-6-chloroquinolin-2-onyl)-1-Amino-2-Hydroxyindane

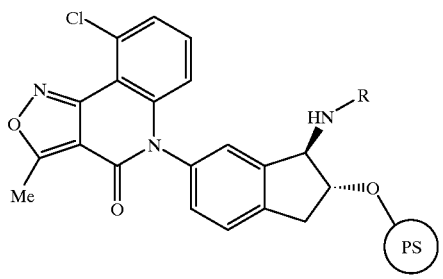

13

Step 1: Installation of the "R" Moiety—Trans O-Resin Bound N-"R"-1-Amino-2-Hydroxy-6-Nitroindane

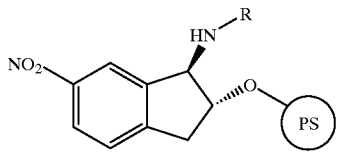

Into a 10 mL round bottom flask was placed trans O-resin bound 1-amino-2-hydroxy-6-nitroindane (0.0283 mmol) followed by 500 μL of a solution of pyridine (36.6 μL, 0.452 mmol) and DMAP (0.518 mg, 0.00424 mmol) in dichloromethane. Next, a 1M solution of a commercially available compound of formula VI, VII, or VIII in dichloromethane (184 μL, 0.184 mmol) was added and the resulting mixture was stirred overnight at 25° C. At this time, the solvent was removed by vacuum filtration and the resin was washed with 50 mL each of dichloromethane, dimethylformamide, methanol, dimethylformamide, methanol, and dichloromethane to give the title compound (compounds of formula X).

Step 2: Reduction—Trans O-Resin Bound 6-Amino-1-((N-"R")-Amino-2-Hydroxyindane

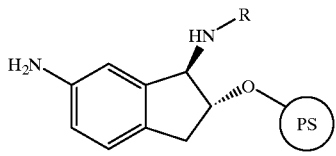

To a solution of trans O-resin bound N-"R"-1-amino-2-hydroxy-6-nitroindane (0.0283 mmol) in dimethylformamide (0.625 mL) was added tin(II)chloride dihydrate (102 mg, 0.452 mmol). Upon stirring at 25° C. for 48 hours, the resin was isolated by filtration and washed with 50 mL each of dichloromethane, dimethylformamide, methanol, dimethylformamide, methanol, and dichloromethane to give the title compound (compounds of formula XI).

Step 3: Acylation—Trans O-Resin bound N-"R"-6-(Isoxazolo[3,4-c]-1,2-Dihydro-3-methyl-6-chloroquinolin-2-onyl)-1-Amino-2-Hydroxyindane

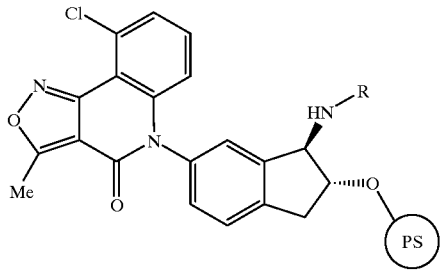

Into a 10 mL round bottomed flask was placed trans O-Resin Bound 6-amino-1-((N-"R")-amino)-2-hydroxyindane (0.0283 mmol) followed by 500 μL of a solution of pyridine (36.6 μL, 0.452 mmol) and DMAP (0.518 mg, 0.00424 mmol) in dichloromethane. Next a 1M solution of 3-(2-chloro-6-fluorophenyl)5-methylisoxaz-4-oyl chloride in dichloromethane (184 μL, 0.184 mmol) was added and the resulting mixture was stirred overnight at 25° C. At this time, the solvent was removed by vacuum

14 filtration and the resin was washed with 50 mL each of dichloromethane, dimethylformamide, methanol, dimethylformamide, methanol, and dichloromethane to give the diacylated product (compound of formula XIII).

Preparations 8–36 correspond to the precursors for Examples 1–29 below.

Preparation 37

Trans-6-Amino-1-((N-t-Butyloxycarbonyl)-Amino)-2-Hydroxyindane

Palladium on carbon (10%, 500 mg) was wetted with methanol then trans-N-t-butyloxycarbonyl-6-nitro-1-amino-2-hydroxyindane (2.63 g, 8.94 mmol) dissolved in 100 mL of methanol was added to it. At 50 psi, an atmosphere of hydrogen was created and maintained in a Parr shaker for about 18 hours. The catalyst was filtered off through talc. and washed with methanol. The methanol was removed in vacuo leaving 2.23 g of the title compound. (94%). MS(FD) m/z 264 (M+). IR(CHCl$_3$) 3444, 3009, 2983, 1692, 1625 cm$^{-1}$.

Preparation 38

1-(Trans-1-((N-t-Butyloxycarbonyl)-Amino)-2-Hydroxyindan-6-yl)isoxazolo[3,4-c]-1,2-Dihydro-3-methyl-6-chloroquinolin-2-one Trans-1-((N-t-butyloxycarbonyl)-amino)-6-amino-2-hydroxyindane (4 g, 7.97 mmol) was dissolved in 10 mL of 2N sodium hydroxide in methanol and stirred under nitrogen at room temperature for about 18 hours. The reaction was diluted with ethyl acetate, washed with 1N aqueous hydrochloric acid and brine, dried over sodium sulfate, filtered, and concentrated. The residue was crystallized from dichloromethane to give 4.07 g of the title compound. (100%). EA calculated for $C_{25}H_{24}ClN_3O_5$: C, 62.31; H, 5.02; N, 8.72. Found: C, 62.11; H, 5.08, N, 8.65. MS(FD) m/z 481 (M−H).

Preparation 39

1-(Trans-1-Amino-2-Hydroxyindan-6-yl)isoxazolo[3,4-c]-1,2-Dihydro-3-methyl-6-chloroquinolin-2-one Trifluoroacetate 1-(Trans-1-((N-t-butyloxycarbonyl)-amino)-2-hydroxyindan-6-yl)isoxazolo[3,4-c]-1,2-dihydro-3-methyl-6-chloroquinolin-2-one (759 mg, 1.57 mmol) was dissolved in 25 mL of dry dichloromethane and stirred under nitrogen at room temperature. Trifluoroacetic acid (10 mL) was added and the reaction was stirred for 1 hour. The solvents were then removed in vacuo, and the residue was treated with dichloromethane/hexanes to precipitate 850 mg of the title compound. (100%). MS(FD) m/z 381 (M+). IR(KBr) 3058, 2998, 1792, 1657, 1629, 1598 cm$^{-1}$.

EXAMPLES

General Procedure for Examples 1–29

To a flask containing trans O-resin bound N-"R"-6-(isoxazolo[3,4-c]-1,2-dihydro-3-methyl-6-chloroquinolin-2-onyl)-1-amino-2-hydroxyindane (0.0283 mmol) was added a 1M solution of sodium hydroxide in methanol (375 μL, 0.375 mmol) and tetrahydrofuran (400 μL). After stirring at 25° C., the reaction was neutralized with 4M hydrochloric acid in methanol (100 μL, 0.400 mmol) The resin was filtered and the filtrate was concentrated under reduced pressure to provide the compound of Examples 1–29 which gave satisfactory $^1$H NMR and MS(IS) analysis.

Example 1
1-(Trans-1-((N-Acetyl)-Amino)-2-Hydroxyindan-6-yl)isoxazolo[3,4-c]-1,2-Dihydro-3-methyl-6-chloroquinolin-2-one

Example 2
1-(Trans-1-((N-Benzoyl)-Amino)-2-Hydroxyindan-6-yl)isoxazolo[3,4-c]-1,2-Dihydro-3-methyl-6-chloroquinolin-2-one

Example 3
1-(Trans-1-((N-[4-Methylbenzoyl])-Amino)-2-Hydroxyindan-6-yl)isoxazolo[3,4-c]-1,2-Dihydro-3-methyl-6-chloroquinolin-2-one

Example 4
1-(Trans-1-((N-[4-Methoxybenzoyl])-Amino)-2-Hydroxyindan-6-yl)isoxazolo[3,4-c]-1,2-Dihydro-3-methyl-6-chloroquinolin-2-one

Example 5
1-(Trans-1-((N-[4-Fluorobenzoyl])-Amino)-2-Hydroxyindan-6-yl)isoxazolo[3,4-c]-1,2-Dihydro-3-methyl-6-chloroquinolin-2-one

Example 6
1-(Trans-1-((N-[4-Chlorobenzoyl])-Amino)-2-Hydroxyindan-6-yl)isoxazolo[3,4-c]-1,2-Dihydro-3-methyl-6-chloroquinolin-2-one

Example 7
1-(Trans-1-((N-[α-Phenylacetyl])-Amino)-2-Hydroxyindan-6-yl)isoxazolo[3,4-c]-1,2-Dihydro-3-methyl-6-chloroquinolin-2-one

Example 8
1-(Trans-1-((N-[α-(4-Chlorophenyl)acetyl])-Amino)-2-Hydroxyindan-6-yl)isoxazolo[3,4-c]-1,2-Dihydro-3-methyl-6-chloroquinolin-2-one

Example 9
1-(Trans-1-((N-[α-Phenoxyacetyl])-Amino)-2-Hydroxyindan-6-yl)isoxazolo[3,4-c]-1,2-Dihydro-3-methyl-6-chloroquinolin-2-one

Example 10
1-(Trans-1-((N-[2-Phenoxybutanoyl])-Amino)-2-Hydroxyindan-6-yl)isoxazolo[3,4-c]-1,2-Dihydro-3-methyl-6-chloroquinolin-2-one

Example 11
1-(Trans-1-((N-[α-Phenyl-α-Acetoxyacetyl])-Amino)-2-Hydroxyindan-6-yl)isoxazolo[3,4-c]-1,2-Dihydro-3-methyl-6-chloroquinolin-2-one

Example 12
1-(Trans-1-((N-Napthoyl)-Amino)-2-Hydroxyindan-6-yl)isoxazolo[3,4-c]-1,2-Dihydro-3-methyl-6-chloroquinolin-2-one

Example 13
N-n-Butyl-N'-(Trans-2-Hydroxy-6-(Isoxazolo[3,4-c]-1,2-Dihydro-3-methyl-6-chloroquinolin-2-onyl)indanyl Urea

Example 14
N-Cyclohexyl-N'-(Trans-2-Hydroxy-6-(Isoxazolo[3,4-c]-1,2-Dihydro-3-methyl-6-chloroquinolin-2-onyl)indanyl Urea

Example 15
N-Phenyl-N'-(Trans-2-Hydroxy-6-(Isoxazolo[3,4-c]-1,2-Dihydro-3-methyl-6-chloroquinolin-2-onyl)indanyl Urea

Example 16
N-(4-Isopropylphenyl)-N'-(Trans-2-Hydroxy-6-(Isoxazolo[3,4-c]-1,2-Dihydro-3-methyl-6-chloroquinolin-2-onyl)indanyl Urea

Example 17
N-(3-Trifluoromethylphenyl)-N'-(Trans-2-Hydroxy-6-(Isoxazolo[3,4-c]-1,2-Dihydro-3-methyl-6-chloroquinolin-2-onyl)indanyl Urea

Example 18
N-(4-Methoxyphenyl)-N'-(Trans-2-Hydroxy-6-(Isoxazolo[3,4-c]-1,2-Dihydro-3-methyl-6-chloroquinolin-2-onyl)indanyl Urea

Example 19
N-(3-Acetylphenyl)-N'-(Trans-2-Hydroxy-6-(Isoxazolo[3,4-c]-1,2-Dihydro-3-methyl-6-chloroquinolin-2-onyl)indanyl Urea

Example 20
N-(3-(Aminomethylphenyl)-N'-(Trans-2-Hydroxy-6-(Isoxazolo[3,4-c]-1,2-Dihydro-3-methyl-6-chloroquinolin-2-onyl)indanyl Urea

Example 21
N-(3-Carboethoxyphenyl)-N'-(Trans-2-Hydroxy-6-(Isoxazolo[3,4-c]-1,2-Dihydro-3-methyl-6-chloroquinolin-2-onyl)indanyl Urea

Example 22
1-(Trans-1-((N-[3-Nitrophenylsulfonyl])-Amino)-2-Hydroxyindan-6-yl)isoxazolo[3,4-c]-1,2-Dihydro-3-methyl-6-chloroquinolin-2-one

Example 23
1-(Trans-1-((N-[(5-Methylisoxazol-4-yl)sulfonyl])-Amino)-2-Hydroxyindan-6-yl)isoxazolo[3,4-c]-1,2-Dihydro-3-methyl-6-chloroquinolin-2-one

Example 24
N-(3-Trifluorophenyl)-N'-(Trans-2-Hydroxy-6-(isoxazolo[3,4-c]-1,2-Dihydro-3-methyl-6-chloroquinolin-2-onyl)indanyl Isothiourea

Example 25
N-(N-Acetyl-3-Aminophenyl)-N'-(Trans-2-Hydroxy-6-(Isoxazolo[3,4-c]-1,2-Dihydro-3-methyl-6-chloroquinolin-2-onyl)indanyl Isothiourea

Example 26
1-(Trans-1-((N-[Furan-2-oyl])-Amino)-2-Hydroxyindan-6-yl)isoxazolo[3,4-c]-1,2-Dihydro-3-methyl-6-chloroquinolin-2-one

Example 27
1-(Trans-1-((N-[1H-Indol-3-oyl])-Amino)-2-Hydroxyindan-6-yl)isoxazolo[3,4-c]-1,2-Dihydro-3-methyl-6-chloroquinolin-2-one

Example 28
1-(Trans-1-((N-[α-(Thiophen-2-yl)acetyl])-Amino)-2-Hydroxyindan-6-yl)isoxazolo[3,4-c]-1,2-Dihydro-3-methyl-6-chloroquinolin-2-one

Example 29
1-(Trans-1-((N-[5-Methylisoxazol-3-oyl])-Amino)-2-Hydroxyindan-6-yl)isoxazolo[3,4-c]-1,2-Dihydro-3-methyl-6-chloroquinolin-2-one MS(FAB) m/z 491 (M+1). $^1$H NMR (CDCl$_3$): δ2.4 (1.8H, s), 2.45 (1.2H, s), 2.85 (1.8H, s), 2.9 (1.2H, s), 3.0–3.1 (1H, m), 3.3–3.5 (1H, m), 4.25 (1H, bs), 4.3–4.4 (0.6H, m), 4.6–4.7 (0.4H, m), 5.3–5.4 (0.4H, m), 5.45.5 (0.6H, m), 6.35 (0.6H, s), 6.42 (0.4H, s), 6.54 (0.4H, d), 6.6 (0.6H, d), 7.15–7.55 (5H, m)

Example 30

1-(Trans-1-((N-[3,4,5-Trimethoxybenzoyl])-Amino)-2-Hydroxyindan-6-yl)isoxazolo[3,4-c]-1,2-Dihydro-3-methyl-6-chloroquinolin-2-one 1-(Trans-1-amino-2-hydroxyindan-6-yl)isoxazolo[3,4-c]-1,2-dihydro-3-methyl-6-chloroquinolin-2-one trifluoroacetate (305 mg, 0.615 mmol) was dissolved in 10 mL of dry dimethylformamide and stirred at room temperature under nitrogen. 3,4,5-Trimethoxybenzoyl chloride (142 mg, 0.615 mmol) was then added followed by triethylamine (187 mg, 1.85 mmol). The reaction was stirred for about 18 hours and worked up as follows: diluted reaction with ethyl acetate and 1N aqueous hydrochloric acid, washed the organic layer twice with 1N aqueous hydrochloric acid, washed the organic layer thrice each with sodium bicarbonate and brine, and dried the organic layer over sodium sulfate. The ethyl acetate was removed and the white solid was triturated with dichloromethane/hexanes to give 275 mg of the title compound. (78%). MS(IS) 576 (M+). EA calculated for $C_{30}H_{26}ClN_3O_7$: C, 62.56; H, 4.55; N, 7.30. Found: C, 62.41; H, 4.40; N, 7.19.

The compounds of the invention are inhibitors of MRP1. Thus, the compounds of the invention may be used to inhibit any neoplasm having intrinsic and/or acquired resistance, conferred in part or in total by MRP1, to an oncolytic or oncolytics. In other words, treatment of such a neoplasm with an effective amount of a compound of this invention will cause the neoplasm to be more sensitive to chemotherapy that was rendered less efficacious by MRP1.

Vincristine, epirubicin, daunorubicin, doxorubicin, and etoposide are oncolytics that are substrates of MRP1. See Cole, et. al., Pharmacological Characterization of Multidrug Resistant MRP-transfected Human Tumor Cells, *Cancer Research*, 54:5902–5910, 1994. Since MRP1 is ubiquitous in mammals, particularly humans, Nooter, K, et. al., Expression of the Multidrug Resistance-Associated Protein (MRP) Gene in Human Cancers, *Clin. Can. Res.*, 1:1301–1310, (1995), chemotherapy whose goal is to inhibit a neoplasm employing any of those agents has the potential to be rendered less efficacious by MRP1. Thus, neoplasms of the bladder, bone, breast, lung(small-cell), testis, and thyroid and more specific types of cancer such as acute lymphoblastic and myeloblastic leukemia, Wilm's tumor, neuroblastoma, soft tissue sarcoma, Hodgkin's and non-Hodgkin's lymphomas, and bronchogenic carcinoma may be inhibited with a combination of one or more of the above oncolytics and a compound of this invention.

The biological activity of the compounds of the present invention was evaluated employing an initial screening assay which rapidly and accurately measured the activity of the tested compound in inhibiting MRP1 or MDR1. Assays useful for evaluating this reversing capability are well known in the art. See, e.g., T. McGrath, et al., *Biochemical Pharmacology*, 38:3611, 1989; D. Marquardt and M. S. Center, *Cancer Research*, 52:3157, 1992; D. Marquardt, et al., *Cancer Research*, 50:1426, 1990; and Cole, et. al., *Cancer Research*, 54:5902–5910, 1994.

Assay for Reversal of MRP1-Mediated Doxorubicin Resistance and MDR1-Mediated Vincristine Resistance: HL60/ADR and HL60/VCR are continuous cell lines, which were selected for doxorubicin and vincristine resistance, respectively, by culturing HL60, a human acute myeloblastic leukemia cell line, in increasing concentrations of doxorubicin or vincristine until a highly resistant variant was attained.

HL60/ADR and HL60/VCR cells were grown in RPMI 1640 (Gibco) containing 10% fetal bovine serum (FBS) and 250 μg/mL GENTAMICIN™ (Sigma) cells were harvested; washed twice with assay medium (same as culture media); counted; and diluted to $2 \times 10^5$ cells/mL in assay medium. Fifty microliters of cells were aliquoted into wells of a 96 well tissue culture plate. One column of each 96 well plate served as a negative control and received assay medium containing no cells.

Test compounds and reference compounds were dissolved in dimethyl sulfoxide (DMSO) at a concentration of 5 mM. Samples were diluted to 20 μM in assay medium and 25 μl of each test compound was added to 6 wells. Assay standards were run in quadruplicate. Twenty-five microliters of 0.4% DMSO was added to four wells as a solvent control. Assay media was added to all wells to achieve a final volume of 100 μl per well.

The plates were incubated at 37° C. for 72 hours in a humidified incubator with a 5% carbon dioxide atmosphere. Cell viability and vitality was measured by oxidation of a tetrazolium salt suing standard conditions. The plates were incubated for 3 hours at 37° C. Absorbance was determined at 490 nm using a microtitre plate reader.

The ability of a test compound to reverse the resistance of HL60/ADR and HL60/VCR cells to doxorubicin was determined by comparison of the absorbance of the wells containing a test compound in addition to the oncolytic (doxorubicin) with the absorbance of wells containing the oncolytic without a test compound. Controls were used to eliminate background and to ensure the results were not artifactual. The results of the assay are expressed as percent inhibition of cell growth. The oncolytic alone at the tested concentration does not usually inhibit the growth of HL60/ADR or HL60/VCR cells.

Representative compounds of formula I demonstrated a significant effect in reversing the MRP1 multiple drug resistance. Many of the compounds showed very significant enhancement of activity in combination with the oncolytic agent as opposed to the oncolytic agent alone. In addition, a large majority of the compounds tested displayed a significant degree of selective inhibition of the HL60/ADR cell line over the HL60/VCR cell line.

When administering an oncolytic in practicing the methods of this invention, the amount of oncolytic employed will be variable. It should be understood that the amount of the oncolytic actually administered will be determined by a physician, in the light of the relevant circumstances, including the condition to be treated, the chosen route of administration, the actual oncolytic administered, the age, weight, and response of the individual patient (mammal), and the severity of the patient's symptoms. Of course, the amount of oncolytic administered should be decided and closely monitored by that patient's physician. After deciding on the oncolytic or oncolytics to employ, *The Physician's Desk Reference*, published by Medical Economics Company at Montvale, N.J. 07645-1742, is a helpful resource to the physician in deciding on amounts of the oncolytic to administer and is updated annually.

Preferred formulations, and the methods of this invention employing those formulations, are those which do not contain an oncolytic. Thus, it is preferred to administer the compounds of this invention separately from the oncolytic. The oncolytics mentioned in this specification are commercially available and may be purchased in pre-formulated forms suitable for the methods of this invention.

The compounds of formula I alone, or optionally in combination with an oncolytic, are usually administered in the form of pharmaceutical formulations. These formulations can be administered by a variety of routes including oral, rectal, transdermal, subcutaneous, intravenous, intramuscular, and intranasal. Such formulations are prepared in a manner well known in the pharmaceutical art and comprise at least one active compound of formula I.

The present invention also includes methods employing pharmaceutical formulations which contain, as the active ingredient, the compounds of formula I, and optionally an oncolytic, associated with pharmaceutical carriers. In making the formulations of the present invention the active ingredient(s) is usually mixed with an excipient, diluted by an excipient, or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound(s) to provide the appropriate particle size prior to combining with the other ingredients. If the active compound(s) is substantially insoluble, it ordinarily is milled to a particle size of less than 200 mesh. If the active compound(s) is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The formulations of the invention can be formulated so as to provide quick, sustained or delayed release of the active ingredient after administration to the patient by employing procedures known in the art.

The formulations are preferably formulated in a unit dosage form, each dosage containing from about 5 to about 100 mg, more usually about 10 to about 30 mg, of each active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The compounds of formula I are effective over a wide dosage range. For example, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

For preparing solid formulations such as tablets the principal active ingredient(s) is mixed with a pharmaceutical excipient to form a solid preformulation composition containing a homogeneous mixture of a compound of the present invention. When referring to these preformulation compositions as homogeneous, it is meant that the active ingredient(s) is dispersed evenly throughout the formulation so that the formulation may be readily subdivided into equally effective unit dosage forms such as tablets, pills and capsules. This solid preformulation is then subdivided into unit dosage forms of the type described above containing from 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The novel formulations which are liquid forms may be incorporated for administration orally or by injection and include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Formulations for inhalation or insufflation include solutions and suspensions in pharmaceutical, aqueous or organic solvents, or mixtures thereof, and powders. The liquid or solid formulations may contain suitable pharmaceutical excipients as described supra. Preferably the formulations are administered by the oral or nasal respiratory route for local or systemic effect. Compositions in preferably pharmaceutical solvents may be nebulized by use of inert gases. Nebulized solutions may be breathed directly from the nebulizing device or the nebulizing device may be attached to a face mask, tent, or intermittent positive pressure breathing machine. Solution, suspension, or powder formulations may be administered, preferably orally or nasally, from devices which deliver the formulation in an appropriate manner.

The following formulation examples are illustrative only and are not intended to limit the scope of the invention in any way. "Active Ingredient(s)" means a compound according to formula I or a pharmaceutical salt or solvate thereof optionally with one or more oncolytics.

Formulation Example 1

Hard gelatin capsules containing the following ingredients are prepared:

| Ingredient | Quantity (mg/capsule) |
|---|---|
| Active Ingredient (s) | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mq/tablet) |
|---|---|
| Active Ingredient (s) | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient (s) | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Active Ingredient (s) | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Active Ingredient (s) | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient (s) | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 mL dose are made as follows:

| Ingredient | Amount |
|---|---|
| Active Ingredient (s) | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
| --- | --- |
| Active Ingredient (s) | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity |
| --- | --- |
| Active Ingredient (s) | 250.0 mg |
| Isotonic saline | 1000 mL |

Formulation Example 10

A topical formulation may be prepared as follows:

| Ingredient | Quantity |
| --- | --- |
| Active Ingredient (s) | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity Per Tablet |
| --- | --- |
| Active Ingredient (s) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the active ingredient is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical formulation to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

We claim:

1. A compound of formula I:

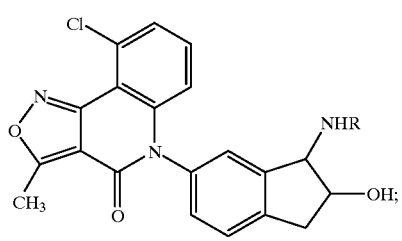

where:

R is hydrogen, $COR^1$, $SO_2R^2$, or a moiety of the formula

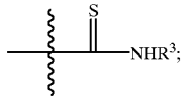

$R^1$ is $C_1$–$C_4$ alkyl, aryl, substituted aryl, furanyl, indolyl, thiophenylmethyl, 5-methylisoxazolyl, $NHR^4$, or $CHR^5OR^6$;

$R^2$ is 3,5-dimethylisoxazolyl or phenyl where the phenyl group is optionally substituted once with nitro, $C_1$–$C_4$ alkyl, trifluoromethyl, $C_1$–$C_4$ alkoxy, $C_2$–$C_4$ alkanoyl, carbo($C_1$–$C_4$ alkoxy), or amino($C_1$–$C_4$ alkyl);

$R^3$ is phenyl where the phenyl group is optionally substituted once with trifluoromethyl or N-acetylamino;

$R^4$ is hydrogen, $C_1$–$C_6$ alkyl, or phenyl where the phenyl group is optionally substituted once with nitro, $C_1$–$C_4$ alkyl, trifluoromethyl, $C_1$–$C_4$ alkoxy, $C_2$–$C_4$ alkanoyl, carbo($C_1$–$C_4$ alkoxy), or amino($C_1$–$C_4$ alkyl);

$R^5$ is hydrogen, $C_1$–$C_4$ alkyl, or phenyl; and $R^6$ is phenyl or acetyl; or a pharmaceutical salt or solvate thereof.

2. The compound according to claim 1 where R is $COR^1$ and $R^1$ is 3,4,5-trimethoxyphenyl.

3. A method of inhibiting MRP1 in a mammal which comprises administering to a mammal in need thereof an effective amount of a compound of formula I:

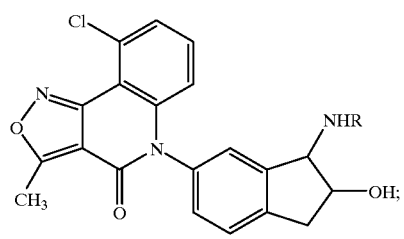

where:

R is hydrogen, $COR^1$, $SO_2R^2$, or a moiety of the formula

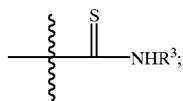

$R^1$ is $C_1$–$C_4$ alkyl, aryl, substituted aryl, furanyl, indolyl, thiophenylmethyl, 5-methylisoxazolyl, $NHR^4$, or $CHR^5OR^6$;

$R^2$ is 3,5-dimethylisoxazolyl or phenyl where the phenyl group is optionally substituted once with nitro, $C_1$–$C_4$ alkyl, trifluoromethyl, $C_1$–$C_4$ alkoxy, $C_2$–$C_4$ alkanoyl, carbo($C_1$–$C_4$ alkoxy), or amino($C_1$–$C_4$ alkyl);

$R^3$ is phenyl where the phenyl group is optionally substituted once with trifluoromethyl or N-acetylamino;

$R^4$ is hydrogen, $C_1$–$C_6$ alkyl, or phenyl where the phenyl group is optionally substituted once with nitro, $C_1$–$C_4$ alkyl, trifluoromethyl, $C_1$–$C_4$ alkoxy, $C_2$–$C_4$ alkanoyl, carbo($C_1$–$C_4$ alkoxy), or amino($C_1$–$C_4$ alkyl);

$R^5$ is hydrogen, $C_1$–$C_4$ alkyl, or phenyl; and $R^6$ is phenyl or acetyl; or a pharmaceutical salt or solvate thereof.

4. The method according to claim 2 where the mammal is a human.

5. The method according to claim 4 where the compound of formula I is a compound where R is $COR^1$ and $R^1$ is 3,4,5-trimethoxyphenyl.

6. A method of inhibiting a resistant neoplasm, or a neoplasm susceptible to resistance, in a mammal which comprises administering to a mammal in need thereof an effective amount of a compound of formula I:

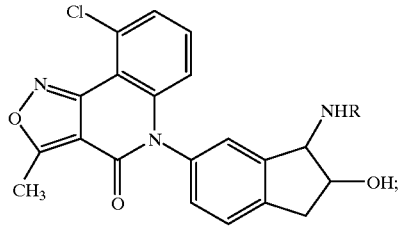

where:

R is hydrogen, $COR^1$, $SO_2R^2$, or a moiety of the formula

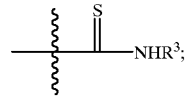

$R^1$ is $C_1$–$C_4$ alkyl, aryl, substituted aryl, furanyl, indolyl, thiophenylmethyl, 5-methylisoxazolyl, $NHR^4$, or $CHR^5OR^6$;

$R^2$ is 3,5-dimethylisoxazolyl or phenyl where the phenyl group is optionally substituted once with nitro, $C_1$–$C_4$ alkyl, trifluoromethyl, $C_1$–$C_4$ alkoxy, $C_2$–$C_4$ alkanoyl, carbo($C_1$–$C_4$ alkoxy), or amino($C_1$–$C_4$ alkyl);

$R^3$ is phenyl where the phenyl group is optionally substituted once with trifluoromethyl or N-acetylamino;

$R^4$ is hydrogen, $C_1$–$C_6$ alkyl, or phenyl where the phenyl group is optionally substituted once with nitro, $C_1$–$C_4$ alkyl, trifluoromethyl, $C_1$–$C_4$ alkoxy, $C_2$–$C_4$ alkanoyl, carbo($C_1$–$C_4$ alkoxy), or amino($C_1$–$C_4$ alkyl);

$R^5$ is hydrogen, $C_1$–$C_4$ alkyl, or phenyl; and $R^6$ is phenyl or acetyl; or a pharmaceutical salt or solvate thereof;

in combination with an effective amount of one or more oncolytic agents.

7. The method according to claim 6 where the mammal is a human.

8. The method according to claim 7 where the oncolytic(s) is selected from the group: doxorubicin, daunorubicin, epirubicin, vincristine, and etoposide.

9. The method according to claim 7 where the neoplasm is a neoplasm of the Wilm's type, bladder, bone, breast, lung(small-cell), testis, or thyroid or the neoplasm is associated with acute lymphoblastic and myeloblastic leukemia, neuroblastoma, soft tissue sarcoma, Hodgkin's and non-Hodgkin's lymphomas, or bronchogenic carcinoma.

10. The method according to any of claims 7–9 where the compound of formula I is a compound where R is $COR^1$ and $R^1$ is 3,4,5-trimethoxyphenyl.

11. A pharmaceutical formulation comprising a compound of formula I:

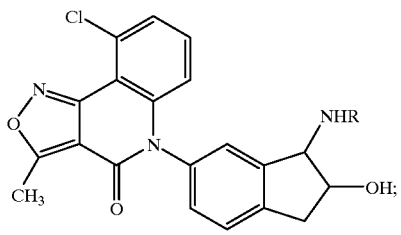

where:

R is hydrogen, $COR^1$, $SO_2R^2$, or a moiety of the formula

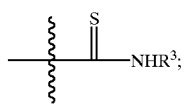

$R^1$ is $C_1$–$C_4$ alkyl, aryl, substituted aryl, furanyl, indolyl, thiophenylmethyl, 5-methylisoxazolyl, $NHR^4$, or $CHR^5OR^6$;

$R^2$ is 3,5-dimethylisoxazolyl or phenyl where the phenyl group is optionally substituted once with nitro, $C_1$–$C_4$ alkyl, trifluoromethyl, $C_1$–$C_4$ alkoxy, $C_2$–$C_4$ alkanoyl, carbo($C_1$–$C_4$ alkoxy), or amino($C_1$–$C_4$ alkyl);

$R^3$ is phenyl where the phenyl group is optionally substituted once with trifluoromethyl or N-acetylamino;

$R^4$ is hydrogen, $C_1$–$C_6$ alkyl, or phenyl where the phenyl group is optionally substituted once with nitro, $C_1$–$C_4$ alkyl, trifluoromethyl, $C_1$–$C_4$ alkoxy, $C_2$–$C_4$ alkanoyl, carbo($C_1$–$C_4$ alkoxy), or amino($C_1$–$C_4$ alkyl);

$R^5$ is hydrogen, $C_1$–$C_4$ alkyl, or phenyl; and $R^6$ is phenyl or acetyl; or a pharmaceutical salt or solvate thereof;

in combination with one or more pharmaceutical carriers, diluents, or excipients therefor.

12. The formulation according to claim 11 where the compound of formula I is a compound where R is $COR^1$ and $R^1$ is 3,4,5-trimethoxyphenyl.

13. A pharmaceutical formulation comprising:
(a) a compound of formula I:

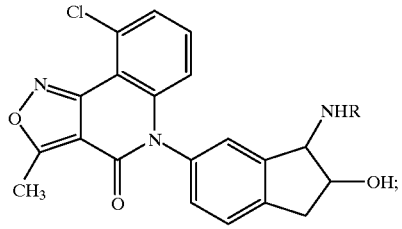

where:
R is hydrogen, $COR^1$, $SO_2R^2$, or a moiety of the formula

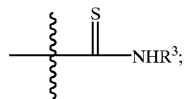

$R^1$ is $C_1$–$C_4$ alkyl, aryl, substituted aryl, furanyl, indolyl, thiophenylmethyl, 5-methylisoxazolyl, $NHR^4$, or $CHR^5OR^6$;

$R^2$ is 3,5-dimethylisoxazolyl or phenyl where the phenyl group is optionally substituted once with nitro, $C_1$–$C_4$ alkyl, trifluoromethyl, $C_1$–$C_4$ alkoxy, $C_2$–$C_4$ alkanoyl, carbo($C_1$–$C_4$ alkoxy), or amino($C_1$–$C_4$ alkyl);

$R^3$ is phenyl where the phenyl group is optionally substituted once with trifluoromethyl or N-acetylamino;

$R^4$ is hydrogen, $C_1$–$C_6$ alkyl, or phenyl where the phenyl group is optionally substituted once with nitro, $C_1$–$C_4$ alkyl, trifluoromethyl, $C_1$–$C_4$ alkoxy, $C_2$–$C_4$ alkanoyl, carbo($C_1$–$C_4$ alkoxy), or amino ($C_1$–$C_4$ alkyl);

$R^5$ is hydrogen, $C_1$–$C_4$ alkyl, or phenyl; and $R^6$ is phenyl or acetyl; or a pharmaceutical salt or solvate thereof;

(b) one or more oncolytic agents; and
(c) one or more pharmaceutical carriers, diluents, or excipients therefor.

14. The formulation according to claim 13 where the oncolytic(s) is selected from: doxorubicin, daunorubicin, epirubicin, vincristine, and etoposide.

15. The formulation according to claim 13 where the compound of formula I is a compound where R is $COR^1$ and $R^1$ is 3,4,5-trimethoxyphenyl.

* * * * *